US007873201B2

(12) United States Patent
Eilbert et al.

(10) Patent No.: US 7,873,201 B2
(45) Date of Patent: Jan. 18, 2011

(54) RECONSTRUCTION OF X-RAY IMAGES INTO BASIS FUNCTION COMPONENTS USING MULTIPLE-ENERGY SOURCES

(75) Inventors: Richard F. Eilbert, Lincoln, MA (US); Kristoph D. Krug, Sudbury, MA (US); John Tortora, Westford, MA (US)

(73) Assignee: L-3 Communications Security and Detection Systems Inc., Woburn, MA (US)

( * ) Notice: Subject to any disclaimer, the term of this patent is extended or adjusted under 35 U.S.C. 154(b) by 1386 days.

(21) Appl. No.: 11/271,196

(22) Filed: Nov. 10, 2005

(65) Prior Publication Data
US 2008/0013819 A1 Jan. 17, 2008

Related U.S. Application Data

(60) Provisional application No. 60/627,081, filed on Nov. 10, 2004.

(51) Int. Cl.
*G06K 9/00* (2006.01)
(52) U.S. Cl. ...................................... 382/141
(58) Field of Classification Search ........................ None
See application file for complete search history.

(56) References Cited

U.S. PATENT DOCUMENTS 6,236,709 B1 * 5/2001 Perry et al. .................... 378/57
6,252,929 B1 6/2001 Swift et al.
6,463,181 B2 10/2002 Duarte
2004/0101097 A1 5/2004 Wakayama et al.

OTHER PUBLICATIONS

International Search Report and Written Opinion of the International Searching Authority in Application No. PCT/US05/40713, Sep. 21, 2006.

* cited by examiner

*Primary Examiner*—Vikkram Bali
*Assistant Examiner*—Elisa M Rice
(74) *Attorney, Agent, or Firm*—Wolf, Greenfield & Sacks, P.C.

(57) ABSTRACT

An inspection system that forms material sensitive X-ray images of items under inspection. The images are decomposed into basis function images using basis functions representative of materials of interest. The decomposed images may be processed separately to detect concentrations of a material of interest corresponding to one or more of the basis functions. When operated in this mode, the inspection system may be used in applications such as material sorting or security screening. At least one basis function is selected to distinguish a material of interest from other materials likely contained with the item, allowing one of the basis function images to be analyzed to obtain information about a specific material of interest. The images may be automatically analyzed or may be superimposed for display with different visual characteristics assigned to the components associated with each basis function for analysis by a human operator.

23 Claims, 4 Drawing Sheets

RECONSTRUCTION OF X-RAY IMAGES INTO BASIS FUNCTION COMPONENTS USING MULTIPLE-ENERGY SOURCES

RELATED APPLICATIONS

This application claims priority under 35 U.S.C. §119(e) to U.S. Provisional Application Ser. No. 60/627,081, entitled "RECONSTRUCTION OF X-RAY IMAGES INTO BASIS FUNCTION COMPONENTS USING MULTIPLE-ENERGY SOURCES," filed on Nov. 10, 2004, which is herein incorporated by reference in its entirety.

FIELD OF INVENTION

This invention relates generally to x-ray imaging and more particularly to identification of materials within an item under inspection.

DISCUSSION OF RELATED ART

X-ray imaging is widely used in many applications. For example, x-ray imaging is used for x-ray diagnosis. It is also used for security inspection systems and in non-destructive evaluation systems. To gain useful information from an X-ray imaging system, data collected by the system must be formatted for display to a human or analyzed by a computer. Therefore, image analysis techniques often are applied to the data before using it for making decisions.

Analysis of x-ray images using basis function decomposition is known. For example, the basic procedure is described by Macovski in U.S. Pat. No. 3,848,130, which is hereby incorporated by reference. Macovski describes basis function decomposition for medical applications, such as differentiating soft tissue from bone.

Eisen et al. describe in U.S. Pat. No. 5,060,249, which is hereby incorporated by reference, a technique for finding lead using K-edge (Ross) filters.

SUMMARY OF INVENTION

In one aspect, the invention relates to a method of operating an inspection system. The inspection system acquires an array of measurements, each measurement representative of a region of a plurality of regions of an item under inspection. The method comprises moving the item under inspection relative to an X-ray data acquisition system to acquire the array of measurements. An array of computed values is formed, each computed value representative of a region of the plurality of regions. The array is formed by computing a plurality of weighting coefficients for each measurement. The weighting coefficients are computed so that the measurement is represented by a combination of a plurality of basis functions, each of the basis functions being weighted in the combination by a respective weighting coefficient of the plurality of weighting coefficients. The plurality of basis functions comprises at least three basis functions, each basis function defining a relationship between a measured parameter and a parameter of operation of the X-ray data acquisition system. Also, each computed value in the array of computed values comprises a weighting coefficient computed for a measurement in the array of measurements, the weighting coefficients in the array being computed for the same basis function of the plurality of basis functions. As part of the method, an inspection decision concerning the item under inspection is made, based at least in part on the at least one array of computed values.

In another aspect, the invention relates to a method of operating an inspection system adapted to acquire an array of X-ray measurements. Each measurement is representative of the X-rays transmitted through a region of an item under inspection. The method comprises forming an array of computed values. Each computed value represents a region of the plurality of regions. The array is formed by computing a plurality of weighting coefficients for each measurement. The weighting coefficients are computed so that the measurement is represented by a combination of a plurality of basis functions, each of the basis functions being weighted in the combination by a respective weighting coefficient of the plurality of weighting coefficients. Each basis function defines a relationship between a measured parameter and a parameter of operation of the inspection system. Also, each computed value in the array of computed values comprises a weighting coefficient computed for a measurement in the array of measurements, the weighting coefficients in the array being computed for the same first basis function of the plurality of basis functions. As part of the method, a quantity of a material of interest present in the item under inspection is identified, based at least in part on the array of computed values, wherein the first basis function represents the material of interest.

In yet a further aspect, the invention relates to a method of operating an inspection system. The method involves acquiring an X-ray image of an item under inspection; identifying from the acquired image a plurality of basis functions representative of the image; and identifying from the identified basis functions at least one material of interest in the item.

BRIEF DESCRIPTION OF DRAWINGS

The accompanying drawings are not intended to be drawn to scale. In the drawings, each identical or nearly identical component that is illustrated in various figures is represented by a like numeral. For purposes of clarity, not every component may be labeled in every drawing. In the drawings.

DETAILED DESCRIPTION

This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Figure 1:
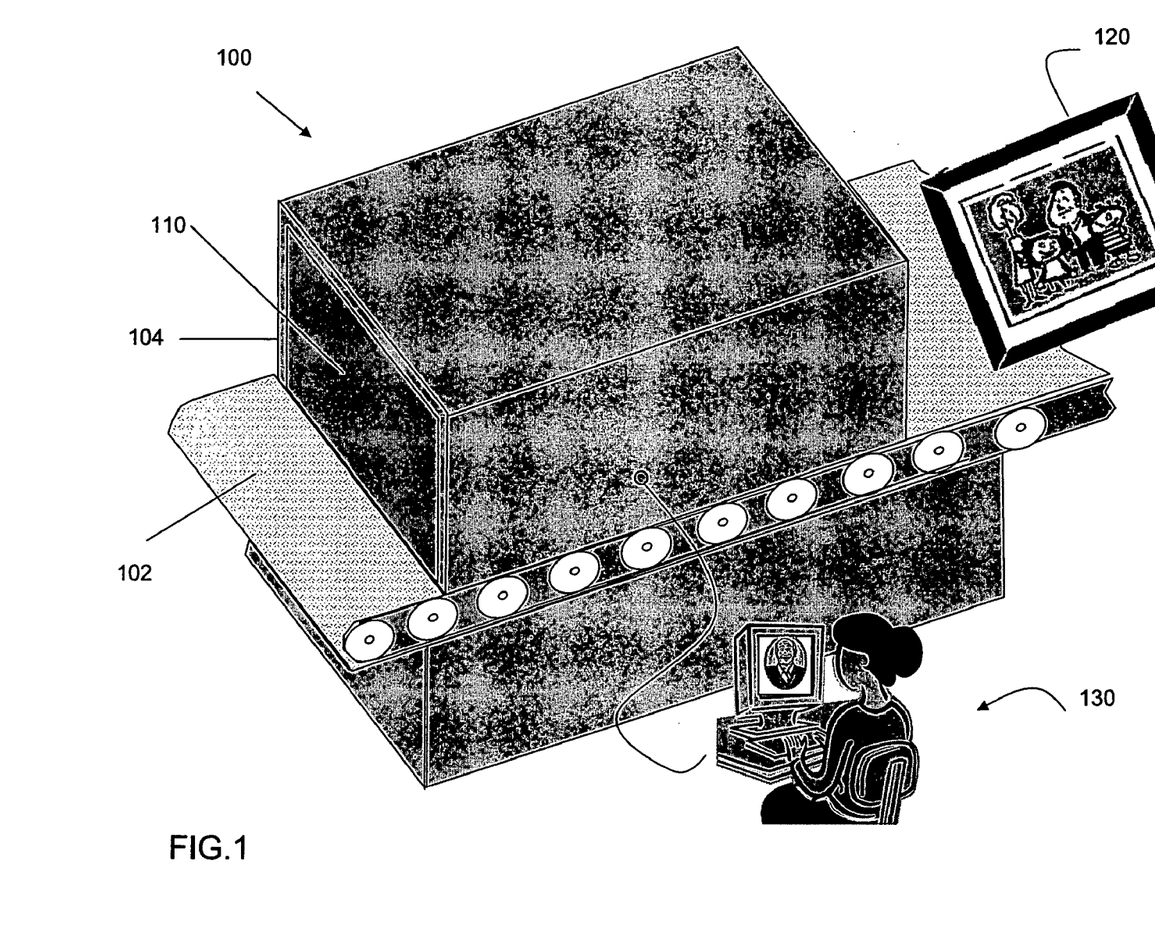
FIG. 1 is a sketch of an x-ray imaging system programmed according to an embodiment of the invention and used to analyze layers of a painting.

FIG. 1 shows an x-ray imaging system 100. X-ray imaging system 100 is here shown to include conveyor 102 and housing 104 that forms tunnel 110. Within tunnel 110, an x-ray source (not shown) generates x-rays. A detector array (not shown) is mounted within tunnel 110 to receive x-rays after they have passed through the item under inspection, which in this case is painting 120. Outputs of the detector array are coupled to an analysis and control station 130.

Analysis and control station 130 contains a computerized data processor, which processes the outputs of the detectors. Analysis and control station 130 also includes a computerized controller which controls the operation of inspection system 100. Though a single device is shown for analysis and control, multiple devices may be used and the analysis and control functions may be distributed over any number of devices in any suitable fashion. Programs for the computerized controller may control the operation of conveyor 102 as well as the x-ray source and detector array. Programmed control may dictate the times at which the x-ray source is turned on and the times at which detectors output data to ensure x-ray image data is collected of items of interest. Data collection operations may be initiated in response to manual inputs or may be performed under program control such that data collection is synchronized to movement of items on conveyor 102.

Programs performing both analysis and control functions may be stored in computer-readable media accessible to a processor within analysis and control station 130. The program may be written in any suitable programming language and may contain one or more components to perform the functions described herein.

In the present example, inspection system 100 includes an x-ray source for which the high voltage applied to the source may be controlled. An x-ray source emits x-rays over a spectrum of energies. However, the voltage level applied to the source will influence the distribution of energies. The x-ray distribution will be skewed towards higher energies as the applied voltage is increased. In the present embodiment, analysis and control station 130 also controls the voltage applied to the x-ray source.

Analysis and control station 130 may be programmed to use basis function decomposition to identify one or more materials that are present in an item under inspection. In the example illustrated in FIG. 1, the item under inspection is a picture 120. In this example, picture 120 is imaged using multiple energy x-rays. The images of picture 120 taken at different energies are spatially correlated to form a combined image with information on attenuation as a function of x-ray energy for each pixel in the image.

Any suitable way may be used to correlate images formed at different energies. The images may be formed in separate passes through an inspection system. Images formed in each pass may then be aligned. However, it is not necessary that each image be formed in a separate pass. Any suitable method of determining the extent to which different regions of the item under inspection attenuate radiation of different energies may be used to create the combined image. In some embodiments, the voltage applied to an X-ray source is varied to change the energy of radiation generated by the source. The applied voltage may be cycled for each measurement such that measurements at multiple X-ray energies are made while the item under inspection is stationary or moves on conveyor 102 only a relatively small amount. In such an embodiment, the images at different energies are spatially correlated by using measurements taken at in the same cycle of applied voltage to represent the same region in the item under inspection.

Regardless of the precise method used to form the combined image, the attenuation versus energy function for each pixel of this combined image is decomposed into basis functions, each basis function representing attenuation as a function of x-ray energy caused by material of a certain type. The decomposition may be used to create multiple decomposed images of picture 120, each representing the distribution of a certain type of material in picture 120.

Where the materials chosen to form the basis functions represent compounds found in different pigments used to form the painting 120, each decomposed image can represent a particular color of paint used to form the picture 120. It has been observed that different colors of paint contain different pigments and that pigments of different colors generally contain different elemental composition. For example, it was observed in a collection of paintings that black paint contained a high level of carbon, yellow paint contained a high level of cadmium, white paint contained a high level of lead. By using measurements on these elements as basis functions to decompose the composite image into basis function images, each basis function image represents a distribution of an element within the item under inspection.

In applying a basis function decomposition analysis, it is not necessary that the basis functions be derived from individual elements. Basis functions can be derived experimentally from measurements on samples of objects of the type to be identified. In the example of a painting to be analyzed, samples of paints of different colors were measured to determine basis functions associated with each color paint.

By selecting appropriate basis functions, basis function decomposition may be used to find objects concealed in or under other objects. In the embodiment depicted in FIG. 1, the "objects" concealed are layers of paint under layers of other paint. Such a technique has been used to analyze a painting that was painted on a canvas previously used for another painting. By performing basis function decomposition on a combined x-ray image of the painting using basis functions derived from paint of different colors, the decomposed images represented layers of paint that are not visible in the final picture 120. By analyzing the decomposed images, the original painting underlying the visible painting could be revealed.

Figure 3A:
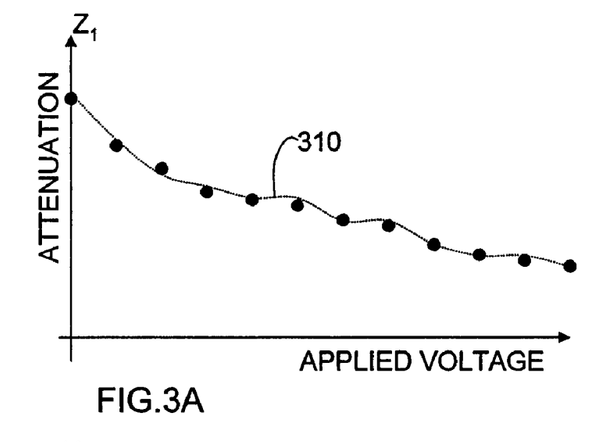
FIGS. 3A and 3B are examples of basis functions.
Figure 3B:
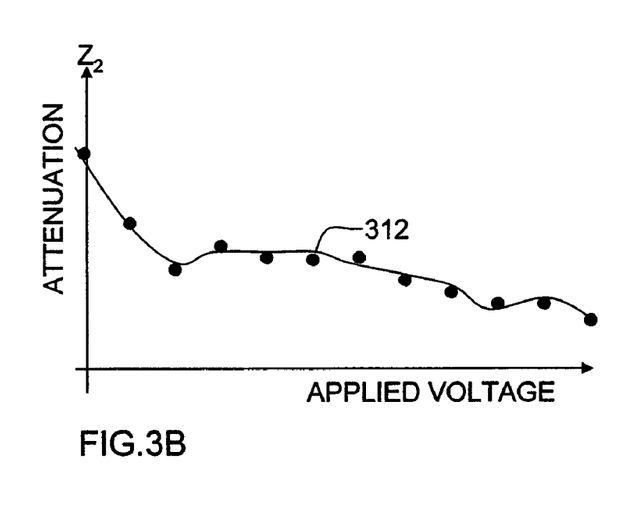

FIGS. 3A-3E illustrate the principles of basis function decomposition. FIGS. 3A and 3B illustrate two basis functions used for decomposition. These functions are selected for illustration. Here, they are selected because they are characteristic of a material of interest believed to be present in an item under inspection. In the described embodiment, an image is decomposed by representing each of its pixels as a linear combination of the basis functions. Accordingly, it may be desirable to use more than two basis functions or to use basis functions other than as pictured.

FIG. 3A shows a basis function 310. Basis function 310 is the attenuation profile for a first material as a function of voltage applied on the x-ray source in the inspection system 100. FIG. 3B is a second basis function 312, which is the attenuation profile for a second material as a function of voltage applied to the x-ray source. Basis functions 310 and 312 are, in this example, formed by measuring the first material and the second material using the x-ray system on which an item under inspection will be imaged.

In FIGS. 3A and 3B, the basis functions are illustrated graphically. Any suitable representation of a basis function may be used. For example, a basis function may be represented as an ordered series of attenuation values stored in a digital data structure in a computer-readable medium in a computer performing image analysis. Representing basis functions as an ordered series of values may be desirable when the basis functions are derived empirically. Where the attenuation versus applied voltage relationship for a material represented by the basis function can be represented as a formula or in other ways, any suitable representation of the basis function may be used.

Additionally, the basis functions shown relate attenuation to applied voltage. Such a basis function is useful in a system that measures attenuation and is controlled through an applied voltage. In this way, the basis function relates the same properties that is conventionally used to create a composite image. More generally, a basis function may define any measurable property in relation to any controllable property that influences the measurable property. For example, the measured property may be intensity, photons per unit time or any other suitable property. Likewise, the controllable property may be x-ray energy, conveyor speed or any other suitable controllable property.

Figure 3C:
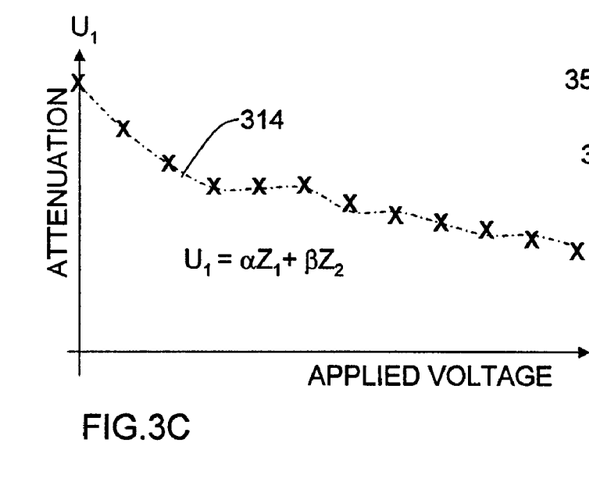
FIG. 3C is an example of an x-ray attenuation curve of a portion of an item with unknown material properties.

FIG. 3C represents a measured attenuation versus energy profile at one pixel of an image of an item under inspection. The attenuation versus applied voltage profile 314 shown in FIG. 3C is formed by taking x-ray measurements at a plurality of energies of an item under inspection. Decomposition of the measured profile 314 is performed by representing the profile 314 as a combination of the two basis functions 310 and 312. Thus the measured profile may be represented by the equation $U_1=\alpha Z_1+\beta Z_2$, where $U_1$ represents the profile measured for one pixel of the item under inspection and $Z_1$ and $Z_2$ are the basis functions. The coefficients $\alpha$ and $\beta$ represent the weightings for the two basis functions required to represent the unknown material. If the material being measured is a combination of the materials used to create the basis functions shown in FIGS. 3A and 3B, the coefficients $\alpha$ and $\beta$ may be taken as a representation of the proportions of those materials in the unknown material.

The coefficients $\alpha$ and $\beta$ may be determined in any suitable way. For example, numerical techniques may be used to compute the value of $\alpha$ and $\beta$ that provide the lowest mean square error in representing the measured curve 314 by a combination of the basis functions 310 and 312. Certain physical constraints may be imposed on the solution. For example, the solution may be constrained to those in which $\alpha$ and $\beta$ are not negative.

One example of numerical techniques that may be used to determine coefficients for respective basis functions is called linear least squares. Though other techniques, such as bounded least squares, may also be used. Additionally, vector processing algorithms may be used. Each measurement and each basis function may be regarded as a vector that is processed according to a least squares technique or any other suitable technique.

Figure 3D:
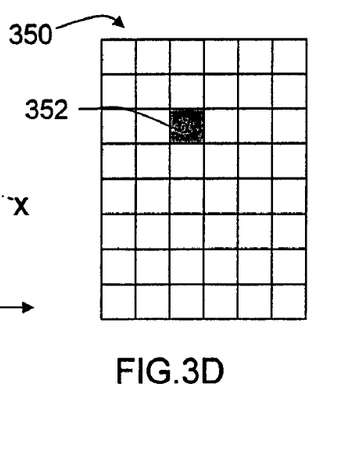
FIGS. 3D and 3E are sketches of basis function images that may be formed using the basis functions of FIGS. 3A and 3B.
Figure 3E:
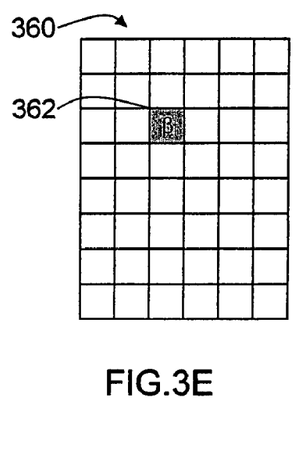

Regardless of how computed, the values of $\alpha$ and $\beta$ can be used to produce pixels in two basis function images. In the example of FIGS. 3A to 3E, each image formed by x-ray system 100 may be decomposed into two images, one representing the amount of the first basis material and the second representing the amount of the second basis material in the item under inspection. FIG. 3D contains an image 350 representing the first basis image and FIG. 3E contains an image 360, representing the second basis image. To decompose the measurement image, each pixel in the composite image formed by inspection system 100 is decomposed into a combination of the basis functions. Accordingly, values of the weightings of these functions, denoted $\alpha$ and $\beta$, may be computed for each pixel in the image. The value of $\alpha$ forms the value of a corresponding pixel in the first basis image 350 and the value of $\beta$ forms the value of a corresponding pixel 362 in the second basis image 360. By computing a value of $\alpha$ and $\beta$ for each pixel in each basis image, a full basis image may be computed.

Though two basis functions are illustrated in FIGS. 3A and 3B, in analyzing an unknown item under inspection, multiple basis function may be used. Each basis function may correspond to a material that may be present in the item under inspection. In some embodiments, more than two basis functions may be used. In some embodiments, a basis function will be used for materials that may appear in significant proportions in the item under inspection. When the technique described herein was applied to a painting, images were formed by basis function decomposition using basis materials such as lead and zinc. These basis materials were selected because they are contained in relatively large proportions in the paint used in creating the painting. Basis function images formed with these basis functions revealed details in the painting that were hidden below the top level of paint.

Figure 2:
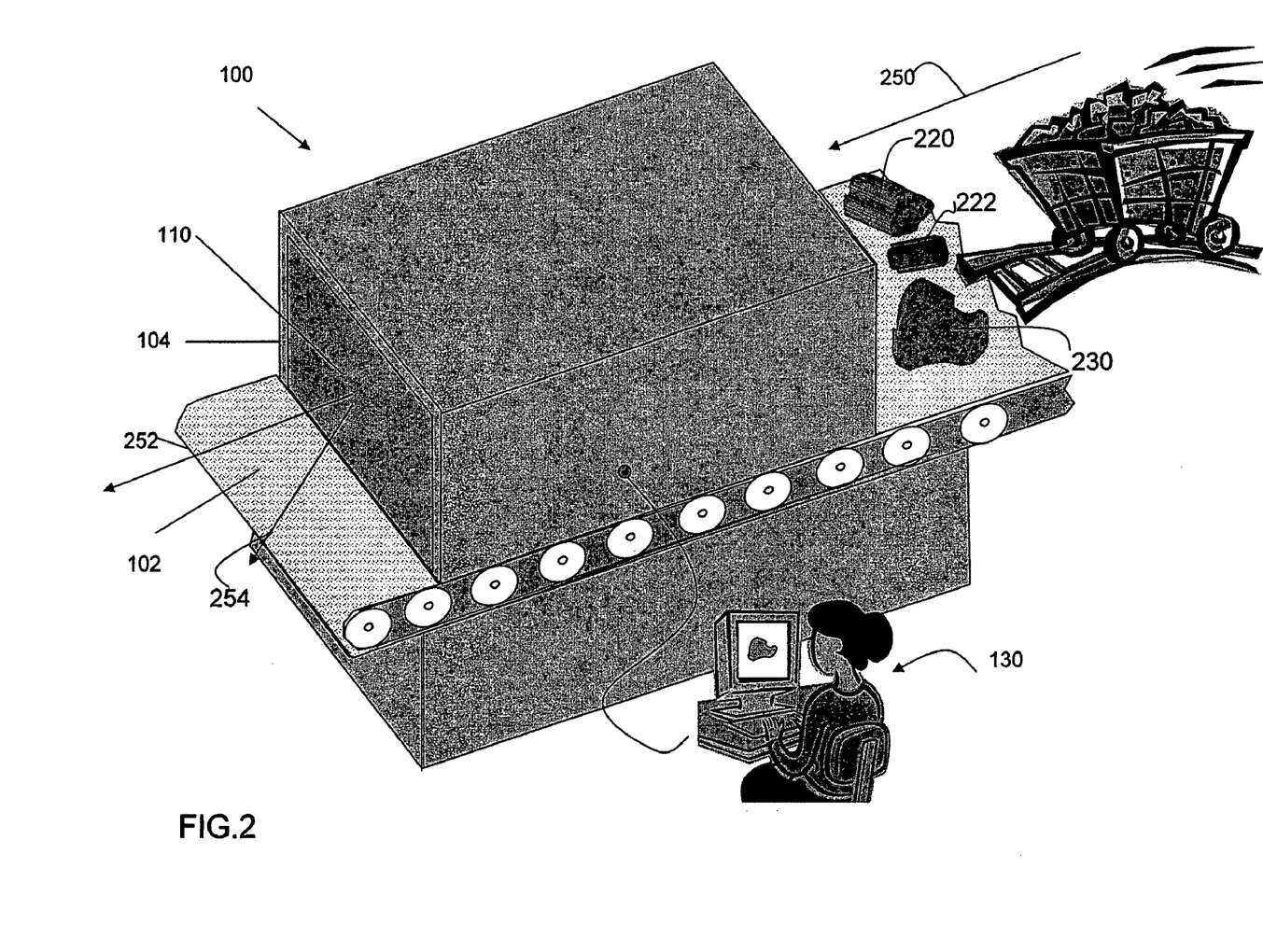
FIG. 2 is a sketch of an x-ray imaging system programmed to identify specific metals mixed in with material on a conveyor.

Basis function decomposition may be used in other ways in other applications. For example, FIG. 2 shows the inspection system 100 used in an ore sorting application. A stream of material 250, which may be material recently mined, is placed on conveyor 102. Stream 250 contains pieces of ore such as 220, 222 and 230 The pieces of ore pass through inspection system 100 where a combined image of the ore, with each pixel of the combined image represents attenuation versus energy, is formed. Basis function decomposition may be used to identify the material components of the ore.

For example, one basis function may be formed using gold as a basis material. Basis function images of the ore may then be formed with control and inspection station 130 programmed to monitor the basis image corresponding to the gold basis function. Control and inspection station 130 may be programmed to look for pieces of ore based on the image. An area of pixels in the gold basis function image having values above a threshold would indicate a piece of ore contains a substantial portion of gold. In this way, the inspection system may be used in an ore sorting operation to identify the pieces of ore that contain specific materials that are to be sorted from the stream of material passing along conveyor 102.

To use inspection system in an ore sorting operation, those pieces of ore identified to have a relatively high gold content would be removed from the stream. One way to remove the gold bearing ore would be to simply divert the stream to a second stream 254 when gold is detected. Otherwise, the ore would continue on in a discard stream 252.

The inspection system 100 may be used in similar applications in which materials are sorted from a stream passing on a conveyor 102. For example, in recycling operations it may be desirable to identify materials containing a high proportion of mercury, cadmium or other harmful metals so that these items may be removed from the recycling stream To identify such materials, images formed with inspection system 100 may be decomposed into basis functions in which some of the basis functions are formed from the attenuation versus voltage profiles for those materials. A similar material identification process may be used in processing streams of refuse or other material in which it is desired to identify a specific material of interest in the stream.

In another embodiment, basis function decomposition may be used on images formed by inspection system 100 in a security screening application. In that application lead or fissionable material, such as uranium or plutonium, may be used as a reference material to form a basis function. In this way, lead or mercury—which may be components of a blasting cap—or even small amounts of fissionable material—which may form a component of a weapon—may be identified.

In applying basis function decomposition, it may be desirable that inspection system 100 produce image information in which attenuation at multiple voltage levels is available for each pixel. There are multiple ways in which such a composite image may be generated. Any suitable manner may be used. For example, the item under inspection may be passed through inspection system 100 multiple times, each time with the x-ray source set to a different voltage level. Where multiple passes are used, attenuation data collected at different passes may be spatially coordinated so that the resulting combined image data contains information about the same pixel imaged at different voltage levels. Alternatively, inspection system 100 may contain a detector array that is sufficiently large to image the entire item under inspection at one time. The item under inspection may stop under the detector array and multiple samples from the detector array taken as the voltage on the source is increased.

In another embodiment, a series of x-ray images of an object of unknown composition is formed. In this embodiment, the images are taken using a cabinet x-ray system with a collimated x-ray source, conveyor and two L-shaped linear arrays of detectors. The detector arrays are adjacent, one being relatively more sensitive to the higher energy (HI) portion of the x-ray spectrum and the other being relatively more sensitive to the lower energy (LO) portion of the x-ray spectrum, due to differences filtration and physical thickness and composition of the arrays. The raw signals from the detectors generated by this cabinet x-ray system are sampled, digitized, corrected for electronic offset and normalized for detector-to-detector gain variability. Each pass of an object through such a system produces two somewhat differing images, the HI image and the LO image.

A series of such images are generated by varying the high voltage to the x-ray tube. Beam current is also varied, but this factor is less important because, apart from image speckliness, its impact is removed by gain normalization. In this embodiment beam high voltage is varied from 50 kVp to 160 kVp but other ranges may be used.

Reference materials are also x-rayed at these same energies to create the basis functions for decomposing the image. In one embodiment, these material consisted of acrylic, aluminum, brass, gadolinium oxysulfide (GOS) and lead (Pb). According to the teachings of Alvarez and Macovski, substantially all the information in the x-ray image can be expressed in terms of a decomposition into the images of two basis materials. Their theory assumes that the x-rays detected are always well above the K-edge transitions in any component element of the object. For typical cabinet x-ray systems used for inspecting baggage, virtually no x-rays of energy below 25 keV are detected due to absorption by the x-ray tube glass and other material in the beam path (e.g. the conveyor belt and detector housing) that result in added filtration. Since the K-edge of copper is at 24 keV, this means that two basis function components (BFCs) suffice to capture the x-ray response for the object's elemental components that have Z less than that of copper. Of course, for alternatively designed x-ray systems, x-rays below 25 keV could be detected and the Z-range of materials represented by Alvarez-Macovski two BFCs would shrink. In this embodiment, elements with Z greater than that of copper (Z=29) form a significant component of the object. In particular, Pb (Z=82) and other high Z elements are present.

The image data from scans of the object at multiple energies provides sufficient information to determine the basis function components of the image. To a good approximation, each attenuation curve scales in direct proportion to the thickness of its respective component. In the present embodiment, the attenuation curves used as the basis functions are via measurement, but such curves may also be obtained by simulation calculations.

It is desirable to register the images taken at the multiple energies, so that in all images, each pixels coordinates refer to the same ray through the object or "x-y point" in the 2D image representation of the object. Each point in the object can be characterized by a series of attenuation values at the various multiple energies. The particular form of this curve can be represented a sum of chosen BFCs weighted by an appropriate amplitude. For example, these amplitudes may be obtained by a least squares fit. The selection of the optimal number and shape of the BFCs will depend on the particulars of the object being analyzed. In some embodiments, inclusion of more than two BFCs for reference materials with atomic number (Z) below copper (in the present embodiment) because this could lead to indeterminacy in the least squares solution. The reference materials may be selected to avoid indeterminacy. Proceeding point-by-point with this analysis, BFC images may be computed. An image of the amplitude level of each of the separate BFCs may be viewed. Such images may indicate, for example, areas of concentration of certain high Z elements, organic material components or metallic components. Moreover, combinations of the BFC images, for example ratios, fractional concentrations, or color-coded summed images, may be useful analytical tools.

Figure 4A:
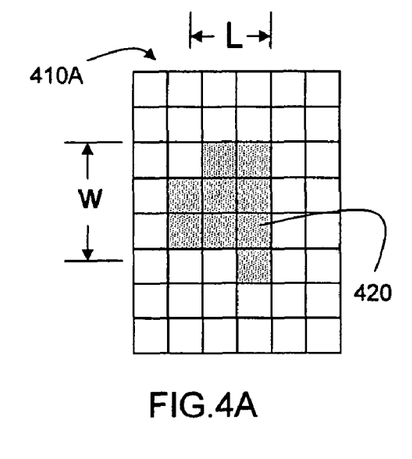
FIGS. 4A, 4B and 4C are basis function images used in an inspection system.
Figure 4B:
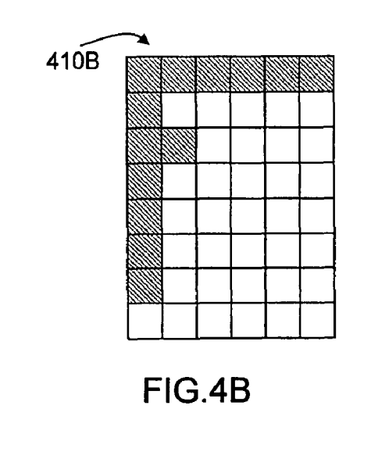
Figure 4C:
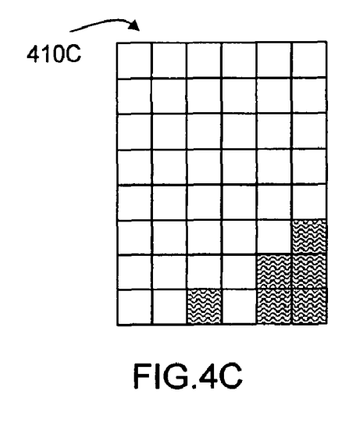

As one example, FIGS. 4A, 4B, and 4C show basis function images 410A, 410B and 410C. At least one of these basis function images may be computed using a basis function representative of a material of interest in a suitcase or package being inspected in a security inspection system. For example, image 410A may be formed with a basis function representative of organic material; image 410B may be formed with a basis function representative of a metallic material; and image 410C may be formed with a basis function representative of high-Z material.

In this context, "high-Z" refers to a material with a K-edge in the range of x-ray energies detected by an inspection system. The precise definition of "high-Z" may therefore be relative to the energy range used by an inspection system. Inspection systems in commercial use today operate at a range of energies such that High-Z equates to an atomic number above about 49. However, if the a system were constructed to operate in an energy range between about 5 to 30 keV, the definition of High-Z would be lower. Alternatively, systems constructed to operate at higher energies, such as cargo container inspection systems that conventionally operate in the 1 to 10 MeV range, would result in a high-Z corresponding to a higher atomic number.

The number of basis functions used to decompose an image and the specific materials selected to represent basis functions may be selected based on the type of materials expected to be in the item under inspection. Every material in the item under inspection will be represented in the decomposed images by coefficients weighting each basis function. The coefficient is in proportion to the similarity between the material in the item under inspection and the material used to form the basis function. Accordingly, to identify a specific material of interest, it is desirable to have a basis function based on a material very similar to the material of interest. Additionally, there should be enough other basis functions that materials in the item under inspection other than the material of interest are primarily mapped to other basis functions.

For example, to detect gold in a material stream that also contains lead, it may be desirable to include two high-Z basis functions, one basis function representative of gold and another representative of lead. In this way, gold and lead may be more readily distinguished. Any number of basis functions may be used, but in some embodiments, each basis function will represent materials that differ in atomic number by at least 5.

The basis function images may be displayed separately, with each pixel having an intensity showing the relative amount of material corresponding to the basis function distributed throughout the item under inspection. Information may be extracted from the basis function images in this fashion. For example, image 410A contains an area 420 with multiple pixels having an intensity above a threshold. Such an area likely corresponds to an object within the item under inspection. The width, W, and length, L, of the area may be measured to determine the size of the object. Other information about the object can be extracted from the images, such as its shape or proximity to other objects.

Figure 4D:
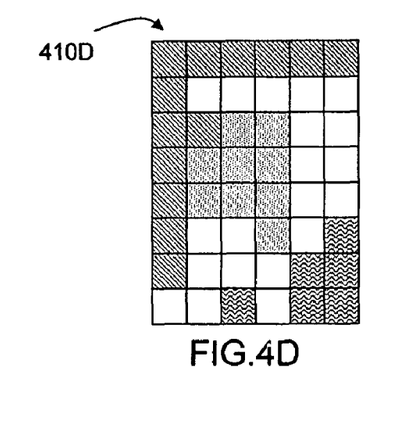
FIG. 4D is a composite image formed from the basis function images of FIGS. 4A, 4B and 4C.

Alternatively, the information from the separate images may be combined. FIG. 4D shows one way in which the information may be combined. In the example of FIG. 4D, the basis function images are combined by superimposing them into a composite image 410D. The contribution from each basis function image is given a visually distinctive characteristic. For example, a color may be associated with each basis function image. In the example of basis function decomposition applied to a painting, each basis function was selected to correspond to a pigment of a specific color. In such an embodiment, the pixels in the basis function images 410A, 410B and 410C could be colored the same color as the pigment they represent. In this way, composite image 410D may appear much like a visual observation of the painting.

However, even when the material corresponding to a basis function does not appear with a meaningful color, the pixels in composite image 410D could nonetheless be color-coded. For example, pixels from a basis function image representing organic materials may be colored green. Pixels from a basis function image representing metallic materials may be colored blue. Pixels from a basis function image representing high-Z materials may be colored orange. In this way, the composite image 410D may display intensities representative of the density of materials present and colors representing the types of material present.

In embodiments described above, basis functions were selected to correspond to specific materials of interest. These basis functions were then used to detect those materials. Such an approach for deriving basis functions is not required. Basis functions could, alternatively, be computed based on measurements for an item under inspection. The basis functions, once determined, could then be analyzed to determine the types of materials that are present.

Principal component analysis may be used to statistically compute the basis functions for decomposition of a particular image. Basis functions from the principal component analysis may be useful in indicating the types of materials present in an item under inspection. Other statistical analysis approaches may be used to generate or select basis functions appropriate to decompose a particular image or class of images.

Principal components analysis is a method of automatically decomposing a data set into a set of basis vectors which are maximally different from each other. These basis vectors are called the principal components. They are also called the eigenvectors. The strengths of each of the components in the basis vector decomposition are called the eigenvalues. Principal components analysis is described in a text, entitled "A User's Guide to Principal Components" by Jackson, which is hereby incorporated by reference in its entirety. To constrain the components to be non-negative, a constrained principal components may be used as described in the Electronic Journal of Linear Algebra ISN1081-3810 published by the International Linear Algebra Society Vol. 10 pp 201-211, which is hereby incorporated by reference in its entirety.

Basis function decomposition may be useful in any situation in which it is desirable to find items containing significant components of a particular element. Alternatively, it may be useful in any situation in which it is desirable to find areas within an item under inspection that contain significant components of a particular element.

Basis function decomposition may also be applied in conjunction with other forms of imaging. For example, if visual inspection of an item reveals that the item has a surface layer of a specific type of material, that surface layer may be modeled as one or more basis function components. These basis function components may then be subtracted from the combined image formed by the inspection system. The remaining image after the surface layer is subtracted out may be further analyzed according to basis function decomposition or in any other suitable manner. Information about surface layers need not be detected by visual inspection. X-ray fluorescence imaging, or any other suitable imaging technique, may be used to detect surface layers.

X-ray fluorescence imaging predominantly forms an image of the surface layer of an item. The image formed by x-ray fluorescence may be used to model the surface layer of an item under inspection. The model of the surface layer may be used to create basis function components representative of the surface layer and can then be subtracted from the image. In this way, basis function decomposition may be used to ignore objects that are not of interest as well as to highlight objects that are of interest.

In a similar fashion, any portion of the item that can be modeled as one or more basis functions may be subtracted from the combined image before further analysis. For example, if the item under inspection rests on a tray that may be characterized, the components in the combined image attributable to the tray may be subtracted from the image before further analysis. In either mode of application, decomposing the image may allow for a more accurate study of the components of the image formed by items in the interior of the item under inspection.

Having thus described several aspects of at least one embodiment of this invention, it is to be appreciated various alterations, modifications, and improvements will readily occur to those skilled in the art.

Examples of embodiments employing basis function decomposition are provided above. Various other embodiments may be made For example, basis functions could be (1) measured BFCs, (2) theoretically computed BFCs, elements or compounds for example or (3) statistically computed BFCs, for example via principal components analysis. Also, it is not necessary that each basis function correspond to a single element, such as lead or gold. Basis functions representing combinations of elements or deamed in other ways may be used.

The series of measurements reflecting response of material to different energy x-rays could be generated by using sources of different energy, filtration to produce different energies from the same source or varying responsiveness of detectors either by filtering or using detectors responsive to different energies. Moreover, each measurement in the series could be made with a single energy or with a spectrum of energies. Any suitable method of generating different energies or different energy spectra for each measurement in the series may be used.

Also, it was described that the item under inspection is held in a specific position as it is imaged at multiple energies. Alternatively, images could be formed at different energies by different sources and then the images may be registered in some way. For example, features in the images could be matched or fiducial marks on a substrate on which the item is positioned may be used for image registration.

Information obtained on an item using basis function decomposition may be combined with information from other images (supplemental information), e.g. visible images or x-ray fluorescence images, to produce a more robust representation of the item under inspection.

Also, it is described that images are presented with intensities proportional to density, as reflected in the measured attenuation. The attenuation may be displayed in "reverse video"—meaning that higher values of attenuation appear brighter. Such a display may be useful, for example, if objects are represented in color.

Further, it is described that images are crated for human observation. All images displayed for humans to observe may alternatively or additionally be analyzed by computer.

Further, adjustments for dependencies of BFCs on attenuation (e.g. hardening), detector position or scatter may be made. For example, values measured with detectors displaced from the center of the x-ray beam may produce different attenuation versus energy profiles. Therefore, different basis functions for those detectors may be required.

Also, the combination of basis functions may not be purely linear. For example, if a beam hardening correction is applied, the basis functions may be adjusted to reflect other materials present in the same pixel that could alter the spectrum of energy reaching the detector.

Also, it is described that the energy of x-rays striking an item under inspection is represented by a voltage applied to the source. While such a control is easy to implement, other ways of controlling or describing the energy spectra may be useful or desirable in some circumstances.

Further, x-rays are described as the type of radiation used. Other types of radiation may be used instead of or in addition to x-rays. For example, gamma rays may be used.

Specific examples of making a decision based on the BFC values (with or without supplemental information) in some region of interest are described above. The BFC values may be used in other contexts to make decisions.

Alternatively, the BFC images may be used to make a composite image (with or without supplemental information). BFC values are described as useful in making BFC images of layers of paint under a painting. A composite image may be formed with this information. Such images may be created by combining information from one or more basis function images, such as by coloring information from different images with different colors. Composite images may be formed in other contexts and used to make decisions, such as in security and inspection applications. The composite images may be formed from BFC images alone or combinations of BFC images and/or visible images and/or fluorescence images and/or information from other sources.

As described above, basis function decomposition is performed on a pixel-by-pixel basis. The output of interest may be a single point, linear or curvilinear array(s), 2D or 3D array(s) (such as might be formed from a tomographic reconstruction)

Such alterations, modifications, and improvements are intended to be part of this disclosure, and are intended to be within the spirit and scope of the invention. Accordingly, the foregoing description and drawings are by way of example only.

We claim:

1. A method of operating an inspection system adapted to acquire an array of measurements, each measurement representative of a region of a plurality of regions of an item under inspection, the method comprising:
   a) moving the item under inspection relative to an X-ray data acquisition system to acquire the array of measurements;
   b) with a computer, forming an array of computed values, each computed value representative of a region of the plurality of regions, the array formed according to a method:
      i) comprising, for each measurement, computing a plurality of weighting coefficients, the weighting coefficients computed so that the measurement is represented by a combination of a plurality of basis functions, each of the basis functions being weighted in the combination by a respective weighting coefficient of the plurality of weighting coefficients;
      ii) wherein:
         A. the plurality of basis functions comprises at least three basis functions, each basis function defining a relationship between a measured parameter and a parameter of operation of the X-ray data acquisition system; and
         B. each computed value in the array of computed values comprises a weighting coefficient computed for a measurement in the array of measurements, the weighting coefficients in the array being computed for the same basis function of the plurality of basis functions;
   c) making an inspection decision concerning the item under inspection based at least in part on the at least one array of computed values.

2. The method of claim 1, wherein the plurality of basis functions comprises at least two basis functions representative of high-Z materials.

3. The method of claim 1, further comprising:
   i) forming a second array of computed values, each computed value in the second array of computed values comprising a weighting coefficient computed for a measurement in the array of measurements, the weighting coefficients in the second array being computed for the same second basis function of the plurality of basis functions; and
   ii) forming a third array of computed values, each computed value in the third array of computed values comprising a weighting coefficient computed for a measurement in the array of measurements, the weighting coefficients in the third array being computed for the same third basis function of the plurality of basis functions.

4. The method of claim 3, further comprising using the array, the second array and the third array to produce an image of the item under inspection.

5. The method of claim 4, further comprising displaying the image, the image being formed as a superposition of the array, the second array and the third array, with each of the array, the second array and the third array having visually distinctive characteristics.

6. The method of claim 5, wherein the visually distinctive characteristics comprise a first color for the array, a second color for the second array and a third color for the third array.

7. The method of claim 3, further comprising using the array, the second array and the third array to make a threat assessment concerning the item under inspection.

8. The method of claim 3, wherein:
i) forming an array comprises forming an array representing a distribution of high-Z material in the item;
ii) forming a second array comprises forming an array representing a distribution of organic material in the item; and
iii) forming a third array comprises forming an array representing a distribution of metallic material in the item.

9. The method of claim 1, wherein each basis function defines a relationship between a measured attenuation and a control voltage on an X-ray tube.

10. The method of claim 1, wherein making an inspection decision comprises automatically deciding that the item under inspection contains a threat object.

11. A method of operating an inspection system adapted to acquire an array of X-ray measurements, each measurement representative of the X-rays transmitted through a region of an item under inspection, the method comprising:
a) with a computer, forming an array of computed values, each computed value representative of a region of the plurality of regions, the array formed according to a method:
i) comprising, for each measurement, computing a plurality of weighting coefficients, the weighting coefficients computed so that the measurement is represented by a combination of a plurality of basis functions, each of the basis functions being weighted in the combination by a respective weighting coefficient of the plurality of weighting coefficients;
ii) wherein:
A. each basis function defines a relationship between a measured parameter and a parameter of operation of the inspection system; and
B. each computed value in the array of computed values comprises a weighting coefficient computed for a measurement in the array of measurements, the weighting coefficients in the array being computed for the same first basis function of the plurality of basis functions;
b) identifying a quantity of a material of interest present in the item under inspection based at least in part on the array of computed values, wherein the first basis function represents the material of interest.

12. The method of claim 11, wherein the item under inspection comprises a stream of material.

13. The method of claim 12, further comprising separating an object from the stream based in part on the quantity of material of interest identified.

14. The method of claim 13, wherein the stream of material comprises a stream of mined material and the object separated from the stream comprises segments of the stream having a quantity of material of interest above a threshold.

15. The method of claim 14, wherein the material of interest consists essentially of gold.

16. The method of claim 13, wherein the stream of material comprises a stream of material to be recycled and the object separated from the stream comprises a segment of the stream having a quantity of material above a threshold.

17. The method of claim 16, wherein the stream of material comprises a waste stream and the object separated from the stream comprise a segment of the stream having a quantity of material above a threshold.

18. The method of claim 17, wherein the material of interest comprises a toxic material.

19. The method of claim 17, wherein the material of interest comprises cadmium.

20. The method of claim 10, further comprising:
i) forming a second array of computed values, each computed value in the second array of computed values comprising a weighting coefficient computed for a measurement in the array of measurements, the weighting coefficients in the second array being computed for the same second basis function of the plurality of basis functions; and
ii) forming a third array of computed values, each computed value in the third array of computed values comprising a weighting coefficient computed for a measurement in the array of measurements, the weighting coefficients in the third array being computed for the same third basis function of the plurality of basis functions.

21. The method of claim 20, wherein:
i) forming an array comprises forming an array representing a distribution of pigment of a first color in the item;
ii) forming a second array comprises forming an array representing a distribution of pigment of a second color in the item; and
iii) forming a third array comprises forming an array representing a distribution of pigment of a third color in the item.

22. The method of claim 21, wherein the item is a painting.

23. The method of claim 10, wherein identifying the quantity of a material of interest present in the item under inspection comprises computing the number of values in the array of computed values having a value above a threshold.

* * * * *